United States Patent [19]

Hansen et al.

[11] 4,271,393
[45] Jun. 2, 1981

[54] APPARATUS AND METHOD FOR EDDY CURRENT DETECTION OF SUBSURFACE DISCONTINUITIES IN CONDUCTIVE BODIES

[75] Inventors: Karl A. Hansen; Iver G. Hendrickson, both of Seattle, Wash.

[73] Assignee: The Boeing Company, Seattle, Wash.

[21] Appl. No.: 974,356

[22] Filed: Dec. 29, 1978

[51] Int. Cl.³ .......................................... G01R 33/12
[52] U.S. Cl. ..................................................... 324/240
[58] Field of Search .............. 324/228, 229, 239, 240, 324/336, 339

[56] References Cited

U.S. PATENT DOCUMENTS

| | | | |
|---|---|---|---|
| 2,527,559 | 10/1950 | Lindblad et al. | 324/336 |
| 2,617,854 | 11/1952 | Van Valkenburg | 324/240 |
| 2,965,840 | 12/1960 | Renken et al. | 324/240 X |
| 3,090,910 | 5/1963 | Moran | 324/339 |
| 3,229,197 | 1/1966 | Renken | 324/240 |
| 3,263,160 | 7/1966 | Dolan et al. | 324/336 |
| 3,359,495 | 12/1967 | McMaster et al. | 324/229 X |
| 4,114,086 | 9/1978 | Kaufman | 324/336 |

Primary Examiner—Gerard R. Strecker
Attorney, Agent, or Firm—Christensen, O'Connor, Johnson & Kindness

[57] ABSTRACT

Nondestructive evaluation of conductive materials is disclosed wherein a magnetic field having a relatively slow rise time and a relatively fast fall time induces eddy currents in the conductive material being tested and subsurface flaws such as internal cracks or other discontinuities are detected by monitoring the magnetic field produced by the eddy currents. The magnetic field is generated by sequentially discharging two capacitor banks through a coil with the currents supplied by the capacitor banks being of opposite polarity and the first capacitive discharge exhibiting a time constant that is substantially longer than the second capacitive discharge. The initial, slowly rising portion of the magnetic field establishes magnetic flux that extends to substantial depths within the conductive material and the fast fall time of the magnetic field causes eddy currents of substantial magnitude to circulate within the region of the conductive material being examined. Flaws within the material cause perturbations in the eddy currents and induce current variations in a pickup coil during a time interval occurring shortly after the magnetic field begins to collapse. Detection equipment, connected for receiving the signal supplied by the pickup coil, monitors the amplitude of the pickup coil signal and, in some situations, its relationship in time relative to the rapid collapse of the magnetic field to determine the presence and location of a flaw.

15 Claims, 6 Drawing Figures

APPARATUS AND METHOD FOR EDDY CURRENT DETECTION OF SUBSURFACE DISCONTINUITIES IN CONDUCTIVE BODIES

BACKGROUND OF THE INVENTION

This invention relates to nondestructive evaluation of conductive materials to detect discontinuities such as cracks, voids and other types of flaws both at and below the surface of such materials. More particularly, this invention relates to detection methods and apparatus for inducing eddy currents into predetermined regions of a metal object and monitoring the magnetic field established by the eddy currents to provide an indication of flaws within the metal object.

It is well-known that eddy currents will be produced in an electrically conductive object that is subjected to a time-varying magnetic field and that such eddy currents establish a magnetic field that interacts with the original magnetic field in a manner which tends to oppose changes in the original field. This principle has been utilized in the prior art in a variety of manners including measurement of the conductivity of metal samples and nondestructive evaluation of conductive materials to detect internal flaws such as cracks or voids and unbonded areas of clad metal objects. In such prior art apparatus for conductivity measurement and nondestructive evaluation, a field generating coil is excited with a sinusoidally varying current or other periodic (CW) signal to produce a corresponding periodically varying magnetic field and the interaction between the magnetic field generated by the excitation signal and the magnetic field established by the eddy currents is detected to determine whether or not a conductive material is free of discontinuities. Generally, such detection is accomplished by monitoring the composite magnetic field by sensing the effect the eddy currents have on the energization signal or by sensing the signal induced in either a secondary winding of the energization coil or a separate coil that is positioned within the composite magnetic field.

Prior art CW eddy current devices exhibit several disadvantages and drawbacks, including relatively poor resolution insofar as the ability of such a device to determine the location of a subsurface discontinuity and relatively poor sensitivity with respect to an ability to detect small subsurface discontinuities such as short hairline cracks that lie a significant distance below the surface of the object being examined. Both of these problems primarily result from the fact that a relatively low frequency energization signal must be used in order to detect discontinuities that lie relatively deep within the material being inspected, i.e., a substantial distance below the surface thereof. That is, as is known by those skilled in the art, as a magnetic field penetrates a conductive material and establishes eddy currents, the magnetic field is exponentially attenuated at a rate that will decrease the flux density to approximately 37% of its original value at a penetration depth that is customarily identified as the "skin depth". Further, it is known that such skin depth is inversely proportional to both the square root of the frequency at which the field varies and the square root of both the material conductivity and permeability. Accordingly, prior art CW detection systems require a low frequency excitation signal in order to establish eddy currents within portions of the material that lie considerably below the surface, especially when materials of relatively high conductivity or permeability are being examined. Although low frequency signals are necessary in order to detect discontinuities that are relatively deep within the material, such low frequency signals are not desirable in that the magnitude of the induced eddy currents is directly proportional to the time rate of change in magnetic flux (Faraday's Law). Thus, although it is necessary to use a low frequency excitation signal in order to effect sufficient penetration of the magnetic field, such low frequency signals do not induce strong eddy current action. Since eddy currents of a relatively high magnitude are necessary so that rather small discontinuities that are relatively deep within the object being inspected will produce easily detectable perturbation or alteration of the magnetic field at the surface of the object being inspected, low frequency CW eddy current inspection devices must operate at relatively high power levels. Even when relatively high power levels are used, presently available CW inspection devices do not exhibit the sensitivity required to detect small discontinuities such as hairline cracks less than 0.5 inches in length that lie on the order of 0.25 inches below the surface of a conductive member.

The use of a low frequency energization signal also affects system resolution in that relatively large coils are generally necessary in order to supply a magnetic field of suitable flux density. In particular, since prior art CW eddy current inspection devices utilize energization currents on the order of several hundred milliamps and operate at relatively high power levels, the drive coils that provide the energizing magnetic field must generally consist of several hundred turns of relatively heavy wire in order to provide a high impedance at the energization frequency while minimizing the resistive component to prevent overheating of the drive coil. Since such coils are relatively large, a magnetic field is supplied to a relatively large region of the conductive material being examined. Thus, although such a system may indicate the presence of a subsurface flaw, the location thereof cannot be accurately determined.

The above-mentioned problems are of special significance in situations in which subsurface flaws are to be detected in conductive material which includes various intended surface features. For example, many structural assemblies such as modern high-speed aircraft employ conductive skin layers that are joined to frame members by the use of various conventional fasteners such as rivets or bolts and are joined together by various splice configurations that employ such fasteners. In maintaining such aircraft and other structures that include multiple layers of conductive material is often necessary and desirable to detect fatique induced cracks or flaws that can develop in one of the subsurface layers, especially along the periphery of the fasteners which join such subsurface layers to other layers of conductive material or various frame members. When prior art CW eddy current inspection techniques are employed in such situations, the relatively large drive coils often induce a magnetic field that encompasses a larger region of the material than is desired. In particular, in many instances the resulting eddy currents will be affected not only by subsurface flaws but by adjoining fasteners, small openings between adjacent pieces of skin material or normal variations in countersunk or counterbored regions of the fastener openings. Thus, oftentimes it is difficult or impossible to determine whether the changes in the magnetic field produced by the induced eddy currents is due to subsurface discontinuities or is due to one of the above mentioned design features.

Various proposals have been made to eliminate or alleviate at least some of the above-discussed disadvantages of prior art CW eddy current inspection devices. For example, U.S. Pat. Nos. 2,965,840 and 3,229,197, issued to C. J. Renken Jr., are illustrative of efforts to utilize periodically pulsed magnetic fields rather than sinusoidally varying fields to induce eddy currents in conductive materials. Such pulse techniques minimize power handling requirements and hence reduce the size of the drive coils to improve resolution. Further, in the apparatus disclosed in the Renken patents, a drive coil is excited with a pulse signal wherein pulses of relatively long-time duration are supplied in alternation with pulses of relatively short-time duration to thereby successively supply magnetic fields which deeply penetrate the material being examined and magnetic fields which penetrate only the surface region of such material. The eddy currents produced by the successive long- and short-duration pulses are then detected and separated from one another and the detected signal that represents the short-duration drive pulse is subtracted from the signal that represents the long-duration drive pulse to supply a signal that is insensitive to spacial variations between the drive coil and the surface of the material being examined. This signal is then utilized to provide an indication of the conductivity of the material being examined and/or subsurface flaws within such material.

Although pulsed techiques such as those disclosed by Renken partially overcome the disadvantages of sinusoidally excited CW eddy current devices, such pulsed techniques still do not provide the sensitivity necessary to detect relatively small cracks or flaws that are located fairly deep within a conductive material. For example, it presently appears that commercially available eddy current devices are incapable of detecting hairline cracks that are less than 0.5 inches in length and lie 0.25 inches or more below the surface of a conductive member. Thus, while prior art eddy current devices may provide satisfactory results in some situations, state-of-the-art limitations prevent application in many important situations. For example, under current design technology, the previously mentioned multilayered aircraft structure can employ a skin layer of 0.25 inches or more in thickness and prior art CW techniques are not satisfactory in detecting fatigue induced cracks or other flaws within the second layer of material. Further, although the pulsed technique disclosed in the Renken patents presumably eliminates a portion of the eddy currents produced at the surface of the material being inspected, such a technique has not proven totally satisfactory in detecting subsurface flaws in the presence of various intended design features. For example and as previously mentioned, when multilayered structure is joined together or joined to other structural members, adjacent edges of the surface panels are often separated by a small gap and the openings for the fasteners are often counterbored or countersunk. Since such boundary edges and fastener features extend entirely through or substantially into the top layer of a multiple layered structure, substantial perturbations in the eddy currents can be produced which, under prior art techniques, cannot be discerned from unintended subsurface flaws.

In addition, the pulsed techniques of the Renken patents and various other approaches that have been utilized to improve performance of prior art eddy current detection devices require rather complicated apparatus for producing signals indicative of the various components of the composite magnetic field and, in effect, separating the eddy currents generated within the conductive material from either the original, energizing signal or the eddy currents generated at the surface of the material. For example, the apparatus disclosed in both of the previously mentioned Renken patents includes rather complex gating circuitry, signal separation and stabilization circuitry and signal compensation circuitry.

Accordingly it is an object of this invention to provide a method and apparatus for inducing eddy currents within conductive structure to determine subsurface flaws that lie deep within a material being examined.

It is another object of this invention to provide a method and apparatus for eddy current detection of subsurface flaws wherein the resolution achieved permits detection of relatively small discontinuities such as relatively short hairline cracks that lie below the surface of the material being examined.

It is yet another object of this invention to provide a method and apparatus for eddy current detection of relatively small subsurface cracks and flaws that are located about the periphery of fasteners that join the adjacent layers of a multilayered structure or form splices between adjacent surface panels.

Still further, it is an object of this invention to provide a method and apparatus of the above-described type wherein subsurface flaws, including those within the interior layers of a multilayered structure, are detectable in the presence of various surface irregularities and structural features.

Even further, it is an object of this invention to provide eddy current inspection apparatus of the above-described type which does not require relatively complex signal processing arrangements and, hence, can be easily and economically produced.

SUMMARY OF THE INVENTION

These and other objects are achieved in accordance with this invention by energizing a conductive material that is to be examined for subsurface discontinuity and flaws with an aperiodic magnetic field having a flux density that first increases at a relatively slow rate and, upon reaching a predetermined maximum flux density, rapidly decreases. During the slowly rising portion of the energizing field, magnetic energy penetrates deep within the conductive material being examined. When the electromagnetic field is rapidly collapsed, eddy currents of substantial magnitude are induced throughout the volume of conductive material subjected to the slowly rising energization field. These eddy currents are sensed at the surface of the conductive material and perturbations therein are detected to thereby detect the presence and approximate size of subsurface flaws. In particular, when examining a specific conductive configuration, the magnetic field that is associated with the induced eddy currents is detected and compared with the magnetic field supplied when identically configured structure that does not contain subsurface flaws is magnetically excited in the same manner. The presence and approximate size of subsurface flaws in the conductive material being examined can then be determined through differences in amplitude and/or phase between these two magnetic fields.

The disclosed embodiments, which are configured for the detection of flaws such as fatique induced cracks that can develop about the periphery of fasteners that join multilayered structures, each include a drive coil for inducing a magnetic field within the conductive region being examined, a signal supply unit for supplying a current pulse to the drive coil, a magnetic flux sensor for detecting the magnetic field and a signal display and analysis unit for analyzing and/or displaying the signal supplied by the magnetic flux sensor. In each arrangement of the invention, the drive coil is substantially cylindrical in geometry and produces a magnetic field in which the lines of flux emanate from and are substantially perpendicular to an annular face of the drive coil that is positioned on top of each fastener region being examined. The signal supply unit supplies a current pulse having a relatively long rise time and a relatively short fall time to thereby establish a single, pulse-like magnetic field that extends downwardly into the fastener and surrounding conductive material. As the magnetic field is caused to rapidly collapse or decay, substantial eddy currents are produced which flow circumferentially around and through the fastener. The composite magnetic field, resulting from the energization field and the magnetic field produced by the eddy currents is detected by the magnetic flux detector, which, in the disclosed embodiment, is a small electrical coil that is positioned within the central opening of the drive coil or between the drive coil and the surface of the conductive material being examined. In the basic arrangement of the invention, the analysis and display unit is a storage-type oscilloscope which displays the signal produced by the magnetic flux detector when the magnetic field is induced in a fastener region being inspected and the signal produced when a flaw-free fastener region of substantially identical structure is energized by the magnetic field. Amplitude and phase differences between these two signals are then utilized to determine the presence and approximate size and location of subsurface fatigue induced cracks or other flaws within the inspected region.

In accordance with the invention, it has been discovered that the initial portion of the eddy current induced magnetic field reflects structural features that lie in or near the surface of the material being examined whereas magnetic field variations which occur somewhat later in time are more indicative of discontinuities that lie deeper within the conductive material. Accordingly, in the practice of this invention, magnetic field variations caused by features such as fastener countersinks and counterbores and edges of the top conductive layer that lie near the fastener being examined can be at least partially eliminated by considering only a discrete portion of the signal produced by the magnetic flux sensor that occurs a predetermined time after the strong eddy currents are produced (i.e., a predetermined time after the magnetic field begins to collapse). For example, when a storage-type oscilloscope is utilized to display the signals supplied by the magnetic flux sensor, the oscilloscope can be triggered by the rapid fall of the energization current and the oscilloscope sweep delayed by an appropriate amount of time to eliminate portions of the signal which primarily represent features lying in or near the surface of the inspected conductive region.

It has also been discovered that the effect of surface irregularities that lie in or near the surface of the material being examined can be further eliminated by considering both the amplitude and phase of the signal supplied by the magnetic flux sensor relative to the amplitude and phase of the signal supplied when a substantially identical structural configuration having no subsurface cracks or flaws is magnetically excited by a system of this invention. More specifically, it has been found that the magnetic flux sensor signal produced when a subsurface crack or flaw is present differs both in amplitude and the time at which the maximum amplitude is attained relative to the signal produced when a substantially identical flaw-free structure is examined. In this regard, it has been found that, although the difference in amplitude between these two signals is primarily indicative of the presence of a subsurface flaw (including the relative depth and relative size), some amplitude variations occur from intended structural features that lie in or near the surface. On the other hand, the difference in time at which the two signals reach maximum amplitude (phase difference) has been found to be primarily indicative of those features in or near the surface of the region being examined. Accordingly, in situations in which a substantial number and/or variety of surface features are present, increased system resolution and accuracy can be attained by considering both the amplitude and phase characteristics of the signal supplied by the magnetic flux sensor.

BRIEF DESCRIPTION OF THE DRAWING

These and other objects and features of the invention will become apparent to one skilled in the art after a reading of the following description, taken together with the accompanying drawing, in which.

DETAILED DESCRIPTION

Figure 1:
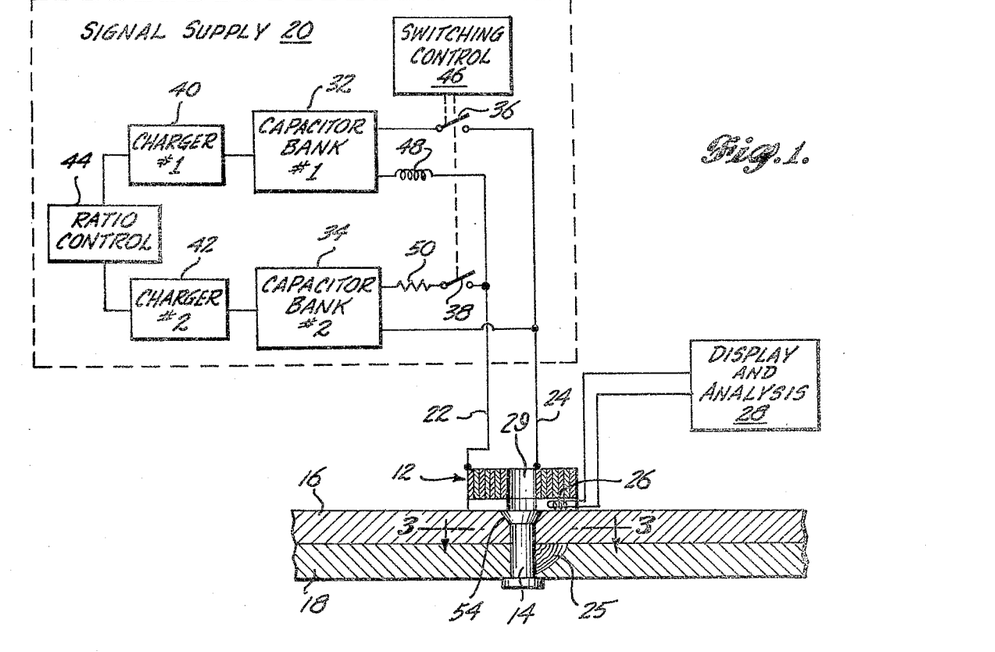
FIG. 1 is a block diagram of an eddy current inspection system of this invention arranged for the examination of fastener regions within a multilayered conductive structure.

FIG. 1 diagrammatically depicts an eddy current inspection system of this invention arranged for the detection of subsurface flaws within multilayered conductive structure. In particular, the eddy current inspection system of FIG. 1 is arranged for the detection of fatigue induced cracks or other discontinuities in subsurface regions that surround conventional fasteners such as rivets or bolts that join two or more sheets of conductive material, interconnect one or more conductive layers to other structures such as frame members, or join two adjacent surface sheets to a lower conductive plate to form a splice or joint. Upon understanding the invention, those skilled in the art will recognize that the embodiment of FIG. 1 is exemplary in nature and that the invention can be arranged and utilized in a variety of situations in which electrically conductive objects are to be examined to detect the presence and/or location of subsurface discontinuities, voids, or flaws. In particular, it will be recognized that the invention has application to a wide variety of situations wherein it is desirable or necessary to locate subsurface features having an electrical conductivity that differs substantially from the normal conductivity of the object being examined. Thus, for example, the present invention can be utilized to determine the position of various internal openings or passages as well as various objects that are covered or surrounded by conductive material and thus, cannot be detected by visual examination.

Referring now more specifically to the arrangement of FIG. 1, a drive coil 12 is symmetrically positioned over a fastener 14 which interconnects an electrically conductive surface sheet 16 with an electrically conductive bottom sheet 18. Energization current for drive coil 12, consisting of a single pulse of current having a relatively long rise time and a relatively short fall time, is supplied by a signal supply 20 that is interconnected with drive coil 12 by means of electrical connections 22 and 24. This current causes drive coil 12 to establish a magnetic field which penetrates into the adjoining region of surface sheet 16 and bottom sheet 18 during the slowly rising portion of the currennt pulse and produces substantial eddy currents that flow circumferentially about fastener 14 as the current pulse rapidly decays in magnitude. These eddy currents, in effect, establish a magnetic field which interacts with the field supplied by drive coil 12. Since the exact paths followed by the induced eddy currents depend on the conductivity of those portions of surface sheet 16 and bottom sheet 18 in which the eddy currents are produced, flaws or other discontinuities within such regions alter the eddy current flow over that produced when regions of surface sheet 16 and bottom sheet 18 that surround fastener 14 are continuous and free from defects. Thus, by comparing the eddy currents associated with the region of conductor containing a discontinuity such as the fatigue induced crack 25 in bottom sheet 18 of FIG. 1 with the eddy currents produced in a substantially identically configured and flaw-free structure, the presence of cracks, voids and other discontinuities can be detected.

In the arrangement of FIG. 1, the eddy currents produced within the region being examined (i.e., that region of surface sheet 16 and bottom sheet 18 that surround fastener 14) are detected by a magnetic flux sensor 26 which supplies an electrical signal to an analysis and display unit 28. More specifically, magnetic flux sensor 26 is positioned near that portion of the surface of surface sheet 16 that is subject to the magnetic field produced by drive coil 12, with magnetic flux sensor 26 being mounted either between drive coil 12 and surface sheet 16 or within an axially extending opening 29 of drive coil 12. In either case, magnetic flux sensor 26 can be any of the various conventional devices which supply an electrical signal when subjected to time-varying magnetic fields. Such devices include, for example, Hall-effect devices and various electrical coils with the coils of the hereinafter described spirally wound, "pancake" variety presently being preferred in that such coils appear to result in the least amount of magnetic coupling between the magnetic flux sensor 26 and drive coil 12.

Analysis and display unit 28 includes apparatus for comparing the amplitude and phase of the signal produced by magnetic flux sensor 26 during the examination of a portion of surface sheet 16 and bottom sheet 18 that includes a fastener 14 with the signal produced when drive coil 12 induces the same magnetic field into a substantially identical, flaw-free structure. For example, in many situations a conventional storage-type oscilloscope that includes delayed triggering capability is satisfactorily employed as analysis and display unit 28. As described hereinafter, in some situations wherein extreme accuracy and resolution are desired or necessary and/or surface sheet 18 includes various intended features that are not identically oriented and configured relative to each fastener region to be examined, a more precise measurement of the amplitude and phase of the signal supplied by magnetic flux detector 26 can be advantageous.

In accordance with this invention, drive coil 12 can be any of the various types of electrical coils which can be configured to exhibit a relatively low inductance value and produce a magnetic field in which the lines of flux extend axially outward from one region of the coil. Examples of such electrical coils are well-known in the art and include the flat "pancake" coil depicted in FIG. 1 wherein wire or a flat strip of conductive material is spirally wound with adjacent windings or turns being electrically isolated from one another by either a dielectric coating on the conductive material or a thin layer of dielectric material that is interposed between the windings. Since, as described hereinafter, substantial current flows through drive coil 12 during each inspection operation, the resistive component of the impedance presented by drive coil 12 should be minimized to prevent the generation of excessive heat within the drive coil. To provide a low resistance, while simultaneously establishing the drive coil geometry so that the area encompassed by the lower surface of drive coil 12 is compatible with the size of fastener 14, pancake coils utilized in the practice of this invention are preferably formed of conductive strips or ribbons rather than wire. For example, in one embodiment of the invention for inspecting regions of aluminum plates that surround fasteners constructed of aluminum, titanium and steel, various coils are utilized as drive coil 12 wherein each coil consists of approximately 10 to 20 turns of 0.02 inch thick by 0.2 inch wide copper strip. Such drive coils generally have an inside diameter on the order of 0.25 inches, an outside diameter on the order of 1 inch, an inductance value of between 1 and 2 microhenries and a resistance value between 2 and 4 milliohms. As shall be described relative to FIG. 4, solenoidal coils are also suitable for use as drive coil 12 and often are preferred in that the magnetic flux produced by such a solenoidal coil is somewhat more orthogonal to the face of the coil that is positoned adjacent to the upper surface of surface sheet 18 than is the magnetic flux produced by other types of coils such as the spirally wound pancake coils. Orthogonal orientation between the supplied magnetic flux and surface sheet 16 and bottom sheet 18 is often desirable in that the induced eddy currents are thereby restricted to a more localized region of the object being inspected.

Figure 2A:
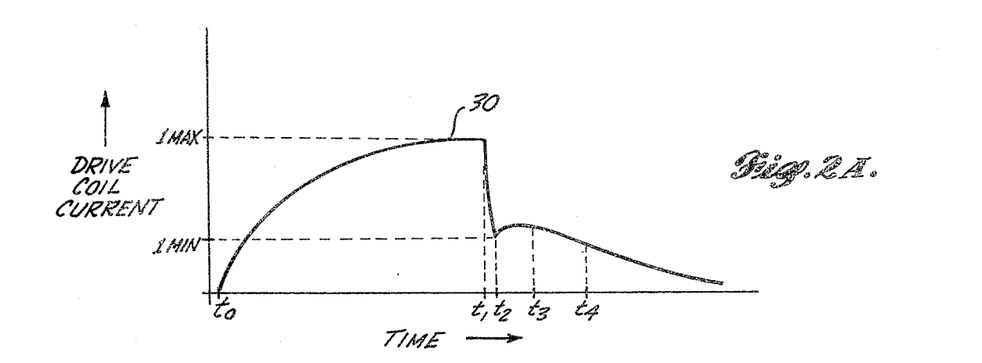
FIGS. 2a and 2b depict typical encountered in the practice of the invention with FIG. 2a illustrating a typical current pulse utilized to establish the magnetic field that induces the eddy currents and FIG. 2b illustrating a typical signal supplied by the magnetic flux sensor.

Regardless of the type of drive coil 12 utilized, signal supply 20 includes circuitry for supplying a drive current having the characteristics depicted in FIG. 2a. In particular, the current pulse 30 of FIG. 2a first slowly increases in magnitude (between times $t_0$ and $t_1$ in FIG. 2) and then rapidly decreases in magnitude between times $t_1$ and $t_2$. Generally, the maximum current ($I_{max}$) of current pulse 30 is on the order of 100 to 1,000 amperes, with the particular value utilized being selected in view of the thickness of the structure being inspected. For example, it has been found generally satisfactory to utilize maximum currents on the order of 250 amperes for detecting fatigue induced cracks that lie within approximately 0.25 inches of the surface of an aluminum structure whereas a maximum current on the order of 750 amperes has been found to be more satisfactory in detecting fatigue induced cracks at depths of around 0.5 inches. Generally, a rise time of approximately 1 to 5 milliseconds is utilized by supply a magnetic field which penetrates deeply into or through the structure being examined without overheating the drive coil 12.

Both the fall time of current pulse 30 ($t_2-t_1$) and the amount of current change ($I_{max}-I_{min}$) is selected in view of the type of material being inspected and its thickness. More specifically, since the eddy currents induced in surface sheet 16 and bottom sheet 18 are substantially proportional to the time rate of change in magnetic flux produced by the rapidly decreasing portion of current pulse 30, relatively short fall times on the order of 10 to 100 microseconds have been found to be most satisfactory. In this regard, fall times of 10 to 30 microseconds are often utilized and the optimum fall time of current pulse 30 can often be selected on the basis of the electrical conductivity and magnetic permeability of the particular type of fastener 14 employed as compared to the electrical conductivity and magnetic permeability of surface sheet 16 and bottom sheet 18. In particular, in applications wherein fastener 14 exhibits a lower conductivity or permeability than surrounding regions of the structure, faster fall times usually produce the best results. For example, in examining fastener regions in aluminum structure, a faster fall time is utilized when the fastener 14 is constructed of titanium (having a conductivity on the order of 30 times less than that of aluminum) than when the fastener 14 is also constructed of aluminum or is constructed of steel (which exhibits relatively low conductivity but a relatively high permeability). In any case, as depicted in FIG. 2a, current pulse 30 need not decrease to zero to produce satisfactory eddy current operation. In fact, when the fastener 14 is constructed of highly permeable materials such as magnetic steel, maintaining a value of $I_{min}$ that causes drive coil 12 to supply a magnetic field that maintains the fastener 14 in a magnetically saturated state can be advantageous. In particular, in such situations wherein the magnetic field produced by $I_{max}$ is sufficiently higher than that required to magnetically saturate a fastener 14, allowing current pulse 30 to decrease below the value which causes saturation may give rise to magnetic field perturbations that tend to mask out or interfere with the perturbations caused by cracks and other subsurface irregularities.

With continued reference to the arrangement of FIG. 1, those skilled in the art will recognize that a variety of circuit arrangements can be employed within signal source 20 to generate the above described current pulse 30. As depicted in FIG. 1, one convenient arrangement, which generally corresponds to the portable power supply disclosed in our copending patent application, Ser. No. 864,735, filed Dec. 27, 1977 and assigned to the assignee of this invention (issued as U.S. Pat. No. 4,148,091 on Apr. 3, 1979), includes first and second capacitor banks (32 and 34) which are selectively discharged through drive coil 12 by means of logic controlled switches 36 and 38. More specifically, in the signal supply arrangement of FIG. 1, capacitor bank 32 and capacitor bank 34 are respectively charged by chargers 40 and 42 prior to the initiation of each current pulse. A ratio control unit 44, interconnected with chargers 40 and 42, controls the voltage to which capacitor banks 32 and 34 are charged so that the desired values of $I_{max}$ and $I_{min}$ will be attained.

To initiate each current pulse 30, a switching control unit 46 closes switch 36 so that capacitor bank 32 discharges through drive coil 12 via electrical connections 22 and 24. For example, switch 36 can be a conventional manually operated switch which completes the indicated circuit path and simultaneously energizes switching logic 46 for subsequent activation of switch 38. A blocking inductor 48, having an inductance value which results in the desired rise time, is connected in series between capacitor bank 32 and drive coil 12. As the current pulse 30 reaches $I_{max}$ (or shortly thereafter), switching control unit 46 closes switch 38 to discharge capacitor bank 34 through drive coil 12 with the current supplied by capacitor bank 34 being opposite in polarity relative to that current supplied by capacitor bank 32. Thus, activation of switch 38 causes the current through drive coil 12 to rapidly decrease with a resistor 50, connected in series with capacitor bank 34 and drive coil 12 establishing the fall time of current pulse 30. Those in the art will recognize that various conventional circuit arrangements can be utilized in switching control unit 46 to cause the activation of switch 38 in the above described manner. For example, switching control 46 can include conventional timing circuits that activate switch 38 a predetermined time after the activation of switch 36 or can include circuitry for detecting the time at which current pulse 30 reaches $I_{max}$.

During the discharge of capacitor bank 32, i.e., the slowly rising portion of current pulse 30, drive coil 12 establishes a slowly increasing magnetic field which pentrates deeply into or through the fastener 14 and surrounding regions of surface sheet 16 and bottom sheet 18. Since drive coil 12 is positioned symmetrically above fastener 14 and is of limited surface area, this magnetic field is effectively confined to the fastener 14 and, in some cases, that region of surface sheet 16 and bottom sheet 18 that immediately surround fastener 14. Since the direction of the magnetic flux produced by drive coil 12 is primarily orthogonal to the surface of conductive sheets 16 and 18, the slowly increasing flux produces eddy currents which circulate circumferentially about the periphery of fastener 14 and within fastener 14 itself. Thus, with respect to surface sheet 16 and bottom sheet 18, an annular region of circulating eddy currents is established that surrounds fastener 14. However, because of the relatively slow rise time of current pulse 30, the magnetic field strength produced by drive coil 12 increases at a rate which does not induce strong eddy currents and, if current pulse 30 remains at $I_{max}$ for a short period of time, the eddy currents produced during this portion of current pulse 30 will subside to substantially zero.

When capacitor bank 34 is discharged through drive coil 12 to produce the rapid fall time of current pulse 30, the magnetic field undergoes a corresponding rapid decrease in flux density to produce strong eddy currents that circulate through and about fastener 14 in a circumferential direction. As is known in the art, these eddy currents produce a magnetic field which tends to sustain the magnetic field originally supplied by drive coil 12, i.e., oppose the change in magnetic field caused by the rapid decrease of current pulse 30. Thus, beginning with the rapid decrease in current pulse 30 at time $t_1$, magnetic flux detector 26 is exposed to a rapidly changing magnetic field which causes flux detector 26 to supply a signal to analysis and display unit 28.

Figure 2B:
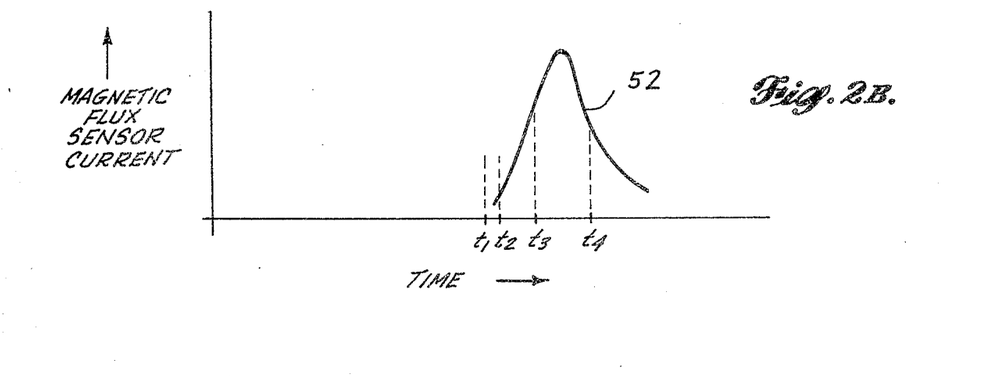
Figures 3, 4:
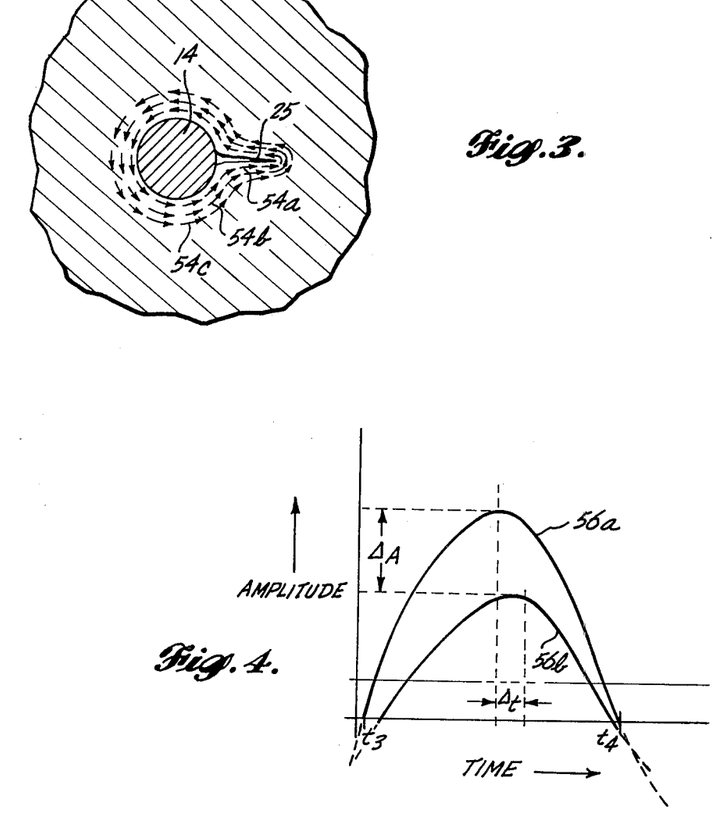
FIG. 3 is a plan view of a fastener opening and subsurface crack which illustrates eddy currents produced in the practice of the invention.
FIG. 4 depicts a portion of two signals supplied by a magnetic flux sensor of this invention to indicate the presence of a subsurface flaw or crack.

FIG. 2b illustrates a typical signal supplied by magnetic flux sensor 26 when drive coil 12 causes the magnetic field to rapidly collapse or decrease in magnitude (i.e., the period time commencing with time $t_1$ in current pulse 30 of FIG. 2a). As can be seen in FIG. 2b and as described above, the rapid decrease in current pulse 30 and accompanying generation of eddy currents within the region of surface sheet 16 and bottom sheet 18 that surrounds fastener 14 causes magnetic flux sensor 26 to generate a rapidly increasing signal (generally denoted by the numerals 52 in FIG. 2b) which reaches maximum magnitude at an instant of time between $t_3$ and $t_4$ and then smoothly decreases. Since, as previously mentioned, the signal induced in magnetic flux sensor 26 is representative of the magnitude of the eddy currents produced, it can be recognized that the maximum amplitude of signal 52 depends on the conductivity of the regions in which the eddy currents are induced. Thus, referring to FIG. 3, which illustrates a plan view taken through a region of bottom plate 18 that includes a fatigue induced crack 25, it can be recognized that cracks or other local discontinuities alter the induced eddy current flow in a manner that is reflected in the maximum amplitude of signal 52. In particular, because of crack 25, the depicted eddy currents 52 cannot flow through bottom sheet 18 along current paths that circumfenentially surround fastener 14. Rather, the eddy currents must pass outwardly around the end of the crack 25 (as depicted in FIG. 3), or must flow above or below the vertical boundaries of the crack. Since, in the presence of such a crack 25, the eddy currents flow around paths that are substantially longer than those that would otherwise be followed, current density within cracked regions of the conductive material is lower than in regions which present uniform conductivity. Further, as is indicated in FIG. 3, when the crack 25 does not extend to a boundary edge of bottom sheet 18, an increase in current density occurs in that portion of bottom sheet 18 that includes the outer terminus of crack 25. This localized increase in current density also contributes to the maximum amplitude and shape of the signal 52.

In the practice of the invention it has been found that the portion of the magnetic sensor signal 52 which immediately follows the rapid decrease in drive current (at time $t_1$) primarily results from various features and discontinuities that lie in or near the surface sheet 16. For example, when fastener 14 is of the countersunk variety depicted in FIG. 1, this portion of signal 52 will be primarily influenced by the size and shape of the countersunk region (region 54 in FIG. 1) and variations in the arrangement of fastener 14 and surface sheet 16 that arise because of manufacturing tolerances in forming the countersunk opening for fastener 14. That is, if the countersunk region 54 extends slightly beyond its nominal design depth, variations in the initial portion of the signall 52 will be introduced relative to the corresponding portion of a signal supplied when the countersunk region 54 is exactly equal to its design value. In this same respect, it has been found that later occurring portions of the signal 52 are less representative of surface irregularities or features and thus are more indicative of flaws that lie relatively deep within surface sheet 16 or within bottom sheet 18. Thus, it has been found advantageously to primarily rely on a portion of signal 52 which occurs a predetermined time after the current through drive coil 12 is caused to rapidly decrease, e.g., the time interval $t_3$-$t_4$ in FIG. 2b. For example, when surface sheet 16 and bottom sheet 18 are constructed of aluminum alloy, time intervals on the order of 100 microseconds which occur from 300 to 1,000 microseconds after initiation of the rapid decrease in current through drive coil 12 have proven satisfactory in detecting hairline cracks as small as 0.2 inches in length and at depths as great as 0.5 inches below the surface of surface sheet 18.

As previously mentioned, monitoring a portion of signal 52 which occurs a predetermined time after the eddy currents are induced can be effected through the use of a storage-type oscilloscope having delayed sweep capabilities as well as a variety of circuit arrangements that lie within the scope of the art. When such signal monitoring is used without implementing additional signal analysis, the signals displayed are similar to those depicted in FIG. 4 wherein the upper wave shape 56a corresponds to a portion of a magnetic flux sensor signal 52 that is associated with a fastener region that does not include a subsurface flaw or crack (such signal being hereinafter denoted as a reference signal) and the lower wave shape 56b corresponds to the identical time period (e.g., $t_3$ to $t_4$ in FIG. 2b) of a magnetic flux sensor signal that is produced when a substantially identically configured fastener region that includes a subsurface crack or flaw is examined. Since, as previously described, the difference between the maximum amplitude of the reference signal 56a and a signal 56b that is supplied in the presence of an internal flaw ($\Delta A$ in FIG. 4) depends on the size and dpeth of the particular crack or flaw, the operator of the system can, based on previous experience, often determine the approximate size and depth of the flaw by observing the amplitude difference A.

Further, as is indicated by FIG. 4, the amplitude versus time characteristic (phase) of magnetic flux sensor signal 56b does not necessarily correspond to the phase characteristic of reference signal 56a in that signal 56b does not always reach its maximum amplitude in the amount of time required for the reference signal 56a to reach its maximum amplitude. Specifically, with respect to the example depicted in FIG. 4, more time elapses before signal 56b reaches its maximum amplitude than elapses before reference signal 56a reaches its maximum amplitude, with the time difference being denoted as $\Delta t$. In the practice of this invention, such a time or phase variation has been found to primarily result from differences in features or discontinuities in or near the surface of surface sheet 16. Thus, for example, if the reference signal 56a is derived from a flaw-free fastener region which does not include any closely adjacent fasteners or boundary edges and the fastener region being examined includes such adjacent features or discontinuities, the signal supplied by magnetic flux detector 26 (e.g., signal 56b of FIG. 4) will exhibit a somewhat different phase characteristic. Similarly, phase differences can be encountered due to variations in the countersink or counterbore of the two fastener regions which result in signals 56a and 56b.

These phase differences often can be important in that, although the above described technique of monitoring the signal amplitude within a predetermined time interval greatly reduces signal variations resulting from structural differences that lie on or near the surface of surface sheet 16, such signal variations are not entirely eliminated. Thus, by additionally monitoring or observing the phase shift between the reference signal 56a and the signal associated with a particular fastener region being examined (e.g., time difference $\Delta t$ in FIG. 4), additional system accuracy and resolution can be attained. In this regard, the operator can use his or her experience and training to interpret the combined amplitude and phase information or, in some situations, a series of charts or diagrams applicable to typical structural variations in the type of fastener region being examined can be prepared and utilized as comparison guides. Even further, where extreme system accuracy is necessary or desired, analysis and display unit 28 can include conventional circuitry for precisely detecting the amplitude and phase of the reference signal 56a and comparing such amplitude and phase with the amplitude and phase of subsequent signals 56b that are generated as each fastener region is inspected. For example, conventional "peak picking" circuitry and timing circuits can be satisfactorily employed.

In any case, the amplitude and phase differences obtained can be displayed on digital display units, or analysis and display unit 28 can include additional circuitry ranging from basic comparator circuits for energizing "go, no-go" indicators to a microprocessor unit that is programmed to perform various signal analysis and/or correlation routines which, based on the phase and amplitude information predict the depth and size of each detected subsurface crack or flaw.

Because substantial eddy currents are produced in the practice of this invention, especially in those embodiments that utilize a current pulse wherein $I_{max}$ is on the order of 750 to 1,000 amperes and $I_{min}$ is 300 amperes or less, substantial mechanical force is exerted on drive coil 12 as the induced magnetic field is caused to rapidly collapse. Accordingly, drive coil 12 is preferably fabricated to withstand mechanical forces without deformation of the coil windings. Further, for convenience and ease of operation, drive coil 12 and magnetic flux sensor 26 can be combined within a single physical unit such as the combined drive coil-magnetic flux sensor 58 depicted in FIG. 5.

Figure 5:
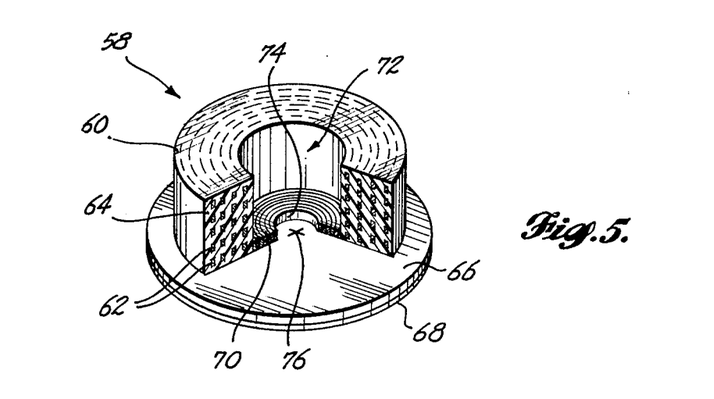
FIG. 5 is a cutaway, isometric view of one embodiment of a drive coil and magnetic flux sensor suitable for use in the system of FIG. 1.

With reference to FIG. 5, the depicted drive coil magnetic sensor 58 includes a solenoidal drive coil 60 formed by spirally winding a conductor 62 in a multilayer solenoidal pattern. To provide structural integrity and rigidty, an encapsulating material 64 fills the regions between adjacent windings and forms a rigid cylindrical body that contains solenoid drive coil 60. The lower face of the drive coil 60 is then bonded, or otherwise attached, to the upper surface of an indexing plate 66 which includes a thin transparent layer 68 bonded to the lower surface thereof.

A spirally wound coil 70, which serves as flux sensor 26 of FIG. 1, is mounted within the lower portion of the axially extending, circular opening 72 of solenoidal drive coil 60 so that the bottom face of the coil 70 is adjacent the upper surface of indexing plate 66. Alternatively, a larger diameter, spirally wound coil that is fabricated of wire can be utilized as the magnetic flux sensor with such coil being interposed between the bottom face of the coil 70 and the upper surface of indexing plate 66. In either case, spirally wound coil 70 and indexing plate 66 can include a central opening 74 that extends downwardly to the transparent layer 68. In such case indexing mark 76, located in transparent layer 68 at the center of central opening 74, allows the combined drive coil-magnetic sensor 60 to be accurately positioned over the fastener of each inspected fastener region.

Those skilled in the art will realize that the embodiments depicted and described herein are exemplary in nature and that many variations can be made without exceeding the scope and the spirit of the invention. For example, rather than directly comparing the magnitude and phase of a reference signal representing the eddy currents produced in a flaw-free fastener region with a signal representing the eddy currents produced in a fastener region being examined, both signals can be resolved into their Fourier components and further signal processing effected to derive an even more accurate determination of the size and depth of each crack or flaw. Thus, it is intended that the claims set forth hereinafter not be deemed restricted to the details of the illustrations as such.

The embodiments of the invention in which an exclusive property or privilege is claimed are defined as follows.

1. Eddy current inspection apparatus for detecting the presence of subsurface regions within a body wherein the region to be detected is of a different electrical conductivity than portions of said body that surround said region to be detected, said eddy current inspection apparatus comprising:

drive coil means positionable on the surface of said body to be inspected, said drive coil means being configured for inducing a magnetic field that is directed inwardly into an inspected region of said body in response to an applied drive signal;

electrical signal supply means interconnected with said drive coil for supplying said drive signal, said electrical signal supplying means including means for supplying said drive signal as a current pulse having a relatively long rise time and a substantially shorter fall time; and magnetic flux detection means positionable on said surface of said body being inspected at a location proximate to said drive coil means, said magnetic flux detection means for supplying a signal representative of the eddy currents produced in said body by that portion of said drive current exhibiting said short fall time.

2. The eddy current inspection apparatus of claim 1 wherein said electrical signal supply means includes means for establishing said rise time within the range of approximately 1 millisecond to approximately 5 milliseconds and means for establishing said relatively short fall time within the range of approximately 10 microseconds to 100 microseconds.

3. The eddy current inspection apparatus of claims 1 or 2 further comprising display and analysis means responsive to said signal supplied by said magnetic flux detection means for detecting and indicating the difference in amplitude between a reference signal supplied by said magnetic flux detection means when said drive coil means is positioned over structure substantially identical to said inspected region of said body which includes no subsurface flaw and each signal supplied by said magnetic flux detection means when said drive coil means is positioned over an inspected region of said body.

4. The eddy current inspection apparatus of claim 3 wherein said apparatus is configured for the detection of subsurface cracks and flaws in the region of a conductive panel surrounding a fastener that extends downwardly into said conductive panel, said drive coil means being configured as a cylindrical electrical coil having an annular face that is symmetrically positionable over the upper end of the fastener of each region to be inspected.

5. The eddy current inspection apparatus of claim 4 wherein said display and analysis means includes means for detecting only a predetermined portion of said signal supplied by said magnetic flux detector which occurs a predetermined time after said fall time of said drive signal.

6. The eddy current inspection apparatus of claim 4 wherein said magnetic flux detection means is a relatively flat, spirally wound electrical coil interposed between said annular face of said drive coil means and the surface of said object being inspected.

7. The eddy current apparatus of claim 4 wherein said magnetic flux detection means is a spirally wound ellectrical coil having an outer diameter commensurate with the diameter of the central opening within said cylindrical electrical coil of said drive coil means, said spirally would electrical coil being mounted in said central opening of said drive coil means at a position adjacent said annular face thereof.

8. The eddy current apparatus of claim 4 wherein said analysis and display means further includes means for detecting and indicating the phase difference between said reference signal and each signal supplied by said magnetic flux detection means when said drive coil is positioned over a fastener within a region to be inspected.

9. A method for detecting subsurface flaws within a conductive body comprising the steps of:
inducing a slowly rising magnetic field into a region of said conductive body that is to be examined for said subsurface flaws with the flux lines of said magnetic field extending inwardly into said conductive body;
rapidly collapsing said induced magnetic field to generate substantial eddy currents which circulate through said region of said conductive body being examined;
monitoring the magnetic field variations caused by said eddy currents to supply a detection signal representative of the magnetic field variations caused by said eddy currents; and
comparing said detection signal with a reference signal which results when said induced magnetic field is introduced into a flaw-free conductive body having substantially the same geometry as said region of said conductive body being examined.

10. The method of claim 9 wherein said step of comparing said detection signal with said reference signal comprises the step of determining the difference between the maximum amplitude of said detection signal and said reference signal.

11. The method of claim 10 wherein said step of comparing said detection signal with said reference further comprises determining the difference in phase between said detection signal and said reference signal.

12. The method of claims 9, 10 or 11 wherein said step of monitoring comprises monitoring said magnetic field variations caused by said eddy currents over a predetermined time interval occurring a predetermined time after said induced magnetic field is rapidly collapsed and wherein said step of comparing said detection signal with said reference signal comprises comparing said detection signal supplied during said predetermined time interval with that portion of said reference signal generated within an identical time interval.

13. The method of claim 12 wherein said step of inducing said magnetic field comprises the step of directing said magnetic field downwardly and through a conductive fastener that joins two or more conductive layers within said conductive body.

14. The method of claim 12 wherein said step of inducing said slowly rising magnetic field includes the step of discharging a first capacitor through a first electrical coil that is positioned over said region of said conductive body that is to be examined and said step of rapidly collapsing said induced magnetic field including the step of discharging a second capacitor through said first electrical coil.

15. The method of claim 12 wherein said step of monitoring said magnetic field variations cuased by said eddy currents includes the step of positioning a second electrical coil adjacent the surface of said region of said conductive body being examined.

* * * * *

UNITED STATES PATENT AND TRADEMARK OFFICE
CERTIFICATE OF CORRECTION

PATENT NO. : 4,271,393
DATED : June 2, 1981
INVENTOR(S) : Karl A. Hansen, et al

It is certified that error appears in the above—identified patent and that said Letters Patent is hereby corrected as shown below:

Column 2, line 53, change "fatique" to -- fatigue --.

Column 6, line 34, Insert -- signals -- before "encountered".

Column 7, line 23, change "currennt" to -- current --.

Column 10, line 35, change "pentrates" to -- penetrates --.

Column 11, line 29, change "circumfenentially" to -- circumferentially --.

Column 11, line 59, change "signall" to -- signal--.

Column 11, line 61, change "value.." to -- value.-- (Delete extra period).

Column 15, line 15, change "ellectrical" to -- electrical --.

Column 16, line 39, change "cuased" to -- caused --.

Signed and Sealed this

Seventeenth Day of November 1981

[SEAL]

Attest:

GERALD J. MOSSINGHOFF

Attesting Officer    Commissioner of Patents and Trademarks